US008496929B2

(12) United States Patent
Xu

(10) Patent No.: US 8,496,929 B2
(45) Date of Patent: Jul. 30, 2013

(54) INOTROPIC EFFECTS OF ANTIBODIES ON CARDIAC CONTRACTION

(76) Inventor: Kai Y. Xu, Cockeysville, MD (US)

(*) Notice: Subject to any disclaimer, the term of this patent is extended or adjusted under 35 U.S.C. 154(b) by 139 days.

(21) Appl. No.: 10/164,363

(22) Filed: Jun. 6, 2002

(65) Prior Publication Data

US 2003/0228315 A1    Dec. 11, 2003

(51) Int. Cl.
*A61K 39/395* (2006.01)
(52) U.S. Cl.
USPC ............... 424/130.1; 424/143.1; 424/146.1
(58) Field of Classification Search
USPC ........................................ 530/131.1, 388.26
See application file for complete search history.

(56) References Cited

PUBLICATIONS

Ovchinnikov et al. Topology of Na+,K+-ATPase. Identification of the extra- and intracellular hydrophilic loops of the catalytic subunit by specific antibodies. FEBS Lett. Jan. 25, 1988;227(2):230-4.*
Mohraz et al. Immunoelectron microscopy of epitopes on Na,K-ATPase catalytic subunit. Implications for the transmembrane organization of the C-terminal domain. J Biol Chem. Jan. 28, 1994;269(4):2929-36.*
Choi et al. Parallel detection of Na,K-ATPase alpha subunit isoforms by pan-specific monoclonal mAb 9A7. Arch Biochem Biophys. Aug. 1, 1997;344(1):165-75.*
Harlow E, Lane D.. Antibodies a laboratory manual. Cold Spring Harbor, New York: Cold Spring Harbor Laboratory Press, 55-135, 1989.*
Owens RJ, Young RJ. The genetic engineering of monoclonal antibodies. J Immunol Methods. 168(2):149-165, 1994.*
Lederman S, et al. A single amino.acid substitution in a common African allele of the CD4 molecule ablates binding of the monoclonal antibody, OKT4. Mol Immunol. 28(11):1171-81, 1991.*
Campbell A, General properties and applications of monoclonal antibodies, Elsevier Science Publishers, section 1.1, pp. 1-32, 1984.*
Bost KL, Pascual DW. Antibodies against a peptide sequence within the HIV envelope protein crossreacts with human interleukin-2. Immunol Invest. 17(6-7):577-86, 1988.*
Bendayan M. Possibilities of false immunocytochemical results generated by the use of monoclonal antibodies: the example of the anti-proinsulin antibody. J Histochem Cytochem. 43(9):881-6, 1995.*
Tamargo et al. Novel therapeutic targets for the treatment of heart failure. Nature Reviews Drug Discovery 10, 536-555 (Jul. 2011).*
Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.*
Colman PM. Effects of amino acid sequence changes on antibody-antigen interactions. Res Immunol. 145(1):33-36, 1994.*
Lederman S, et al. A single amino acid substitution in a common African allele of the CD4 molecule ablates binding of the monoclonal antibody, OKT4. Mol Immunol. 28(11):1171-81, 1991.*
Li Ch, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980.*
Ackermann et al., Biotechnology and Bioengineering, vol. 45, pp. 97-106, 1995.*
William J. Ball, Jr., et al., *Biochimica et Biophysica Acta* :916 100-111 (1987).
Kai Y. Xu, et al., *Biochemical and Biophysical Research Communications* :289 167-172 (2001).
A. C. Myers, et al., *Biochemical and Biophysical Research Communications* :291 111-115 (2002).

* cited by examiner

*Primary Examiner* — Maher Haddad

(57) ABSTRACT

The present invention shows that site-specific antibodies to the ($Na^+ + K^+$)-ATPase exert a potent biological effect in cardiac myocytes and demonstrates a key structural region of the enzyme that participates in the regulation of cardiac contractility. These results establish an important link between a biological action and a precise molecular structure of the ($Na^+ + K^+$)-ATPase. Furthermore, the antibody-induced positive inotropic effect is independent of inactivation of the enzyme may reveal a novel mode for ($Na^+ + K^+$)-ATPase to regulate cardiac function. The data provide new molecular insights into the structural and functional relationship of the ubiquitous ($Na^+ + K^+$)-ATPase.

3 Claims, 5 Drawing Sheets

INOTROPIC EFFECTS OF ANTIBODIES ON CARDIAC CONTRACTION

CLAIM FOR PRIORITY

This application claims the benefit of U.S. provisional patent application Ser. No. 60/275,268 filed Mar. 12, 2001.

FIELD OF THE INVENTION

A novel approach to identify a structural region of the $(Na^++K^+)$-ATPase that is directly involved in regulation of cardiac contractility is provided. Site-specific binding of these antibodies against a known sequence of the $(Na^++K^+)$-ATPase significantly increased the $Ca^{2+}$ transients and contraction of the rat cardiac myocytes. These important findings provide the first connection between the structure of the $(Na^++K^+)$-ATPase and cardiac positive inotropy, wherein a novel mode for $(Na^++K^+)$-ATPase to regulate cardiac function is shown.

BACKGROUND $(Na^++K^+)$-ATPase is a target receptor for digitalis and related drugs. Digitalis, digoxin, ouabain and related substances are cardiac glycosides derived from plants. The main pharmacodynamic property of cardiac glycosides is the ability to increase the force of myocardial contraction in a dose-dependent manner (positive inotropic effect). The most probable explanation for the direct positive inotropic effect is the ability of cardiac glycosides to inhibit membrane-bound $(Na^++K^+)$-activated adenosine triphosphatase $[(Na^++K^+)$-ATPase] (Hoffman, B. F. and J. T. Bigger, Jr., "Digitalis and Allied Cardiac Glycosides" in The Pharmacological Basis of Therapeutics, eds. Goodman and Gilman, p. 732, (1980)). The hydrolysis of adenosine triphosphate (ATP) by this enzyme provides the energy for the sodium potassium pump.

Many researchers have tried to isolate a specific endogenous inhibitor of plasma membrane $Na^+$, $K^+$-ATPase similar to digitalis or ouabain, but of mammalian origin, by measuring immunoreactivity in plasma, to the digoxin radioimmunoassay in situations where the inhibitor might be elevated. The definitive structure of plasma, urinary or tissue inhibitor of $Na^+$, $K^+$-ATPase is not known (Haupert, G. T., Jr., in The $Na^+$, $K^+$-Pump, Part B: Cellular Aspects; Skou, J. C., et al., Eds., p. 297-320 (1988)).

The precise structural region of $(Na^++K^+)$-ATPase that regulates cardiac function is unknown. Hence, relatively little is known about the endogenous regulation of $(Na^++K^+)$-ATPase. Catecholamines (Phillis, J. W., Cell, Tissue and Organ Cultures in Neurobiology, pp. 93-97 (1978); Horwitz, B. A., Fed. Proc., 38:2170-2176 (1979)), thyroid hormone (Smith, T. J. and I. S. Edelman, Fed. Proc., 38:2150-2153 (1979)), aldosterone (Rossier, B. C., et al., Science, 12:483-487 (1987)), linoleic and linolenic acids (Bidard, J. N., et al., Biochem. Biophys. Acta., 769:245 (1984); Tamura, M., et al., J. Biol. Chem., 260:9672 (1985); and vanadium (Cantley, L. C., Jr., et al., J. Biol. Chem., 243:7361-7368 (1978)) have all been linked to either direct or indirect effects on enzyme activity.

Because of their positive inotropic effect, cardiac glycosides (e.g., digitalis and ouabain) are unrivaled in value for the treatment of heart failure. Cardiac glycosides are most frequently used therapeutically to increase the adequacy of the circulation in patients with congestive heart failure and to slow the ventricular rate in the presence of atrial fibrillation and flutter.

However, cardiac glycosides have narrow therapeutic indices and their use is frequently accompanied by toxic effects that can be severe or lethal. The most important toxic effects, in terms of risk to the patient, are those that involve the heart (e.g., abnormalities of cardiac rhythm and disturbances of atrio-ventricular conduction). Gastrointestinal disorders, neurological effects, anorexia, blurred vision, nausea and vomiting are other common cardiac glycoside-induced reactions. Consequently, there is a need in the art for positive inotropic agents which overcome the disadvantages associated with known agents, as well as a need for further information on the mechanisms and receptors associated with cardiac muscle contractility.

It would be highly beneficial to provide patients with a therapeutic composition wherein the cardiac regulatory functions of $(Na^++K^+)$-ATPase are specifically regulated. Moreover, the identification of the key structural regions and amino acids of the $(Na^++K^+)$-ATPase would be of great importance in developing more specific therapeutic molecules, which specifically regulate the cardiac function and differ in characteristics from currently available digitalis glycosides.

SUMMARY OF THE INVENTION

The present invention provides for the identification of the key functional sites of $(Na^++K^+)$-ATPase and also of inotropic agents which directly participate in the regulation of cardiac contraction. In particular, the inotropic agents are antibodies which bind to these functional sites (epitopes) in the α-subunit of $(Na^++K^+)$-ATPase and induce a positive inotropic effect. These novel findings establish the first link between a precise structural region of the $(Na^++K^+)$-ATPase and cardiac positive inotropy.

In particular, the invention provides for purified antibodies which bind to the structural binding site of $(Na^++K^+)$-ATPase and regulate $(Na^++K^+)$-ATPase functions. This is of importance in the treatment of heart disease and other muscle contraction diseases. The antibodies of the invention are polyclonal and/or antisera, monoclonal, and/or humanized antibodies.

The invention also provides for purified antibodies which specifically recognize the amino acid sequences comprising KRQPRNPKTDKLVNE (SEQ ID NO: 1) or VPAISLAYEQAESD (SEQ ID NO: 2) of the -subunit of $(Na^++K^+)$-ATPase enzyme. The binding of the antibodies to these amino acid sequences of the -subunit of $(Na^++K^+)$-ATPase increase cardiac contraction and myocyte intracellular diastolic and systolic calcium.

The antibodies of the invention exert a positive inotropic effect in cardiac myocytes, when they bind to their specific epitopes in the α-subunit of $(Na^++K^+)$-ATPase. The antibodies can be from antisera, polyclonal, monoclonal, and/or humanized antibodies. In a preferred embodiment the antibodies of the invention are used as a therapeutic agent to treat patients suffering from or susceptible to heart disease and/or other muscle contraction disorders.

In particular, the invention provides for purified peptides which are used to generate inotropic antibodies when administered in vivo to a patient, suffering from or susceptible to heart disease and/or muscle contractile disorders. These peptides can be administered individually or in combination in a pharmaceutically acceptable carrier to a patient.

The invention also provides for purified peptides comprising the amino acid sequence KRQPRNPKTDKLVNE (SEQ ID NO: 1) or VPAISLAYEQAESD (SEQ ID NO: 2), which are used to generate inotropic antibodies when administered in vivo to a patient suffering from or susceptible to heart disease and/or myocyte contractile disorders. These peptides can be administered individually or in combination in a pharmaceutically acceptable carrier to a patient.

In accordance with the invention the peptides can be administered in concentrations in a ratio of 1:1 or in varying ratios to each other as defined by their concentration.

In another preferred embodiment, the invention provides for vectors which encode amino acid sequences which are used to generate inotropic antibodies when administered in vivo to a patient suffering from or susceptible to heart disease and/or myocyte contractile disorders. Preferably these vectors are under the control of tissue specific promoters, in particular, cardiac tissue specific. These vectors are also preferably used in generating sera comprising inotropic antibodies using standard methods such as immunizing mammals.

In another preferred embodiment, the invention provides for vectors which encode the amino acid sequence KRQPRNPKTDKLVNE (SEQ ID NO: 1) or VPAISLAYEQAESD (SEQ ID NO: 2), and are used to generate inotropic antibodies when administered in vivo to a patient suffering from or susceptible to heart disease and/or myocyte contractile disorders. Preferably these vectors are under the control of tissue specific promoters, in particular, cardiac tissue specific. These peptides are administered as a vaccine to a patient in need of such therapy, in order to generate endogenous inotropic antibodies.

The amino acids which are encoded by the vector stimulate the immune system to generate antibodies which bind to their epitopes in the α-subunit of $(Na^+ + K^+)$-ATPase, resulting in increased myocyte intracellular diastolic and systolic calcium. These antibodies, exert a positive inotropic effect in cardiac.

In a preferred embodiment, the invention provides for the therapeutic use of antisera, polyclonal and monoclonal antibodies and/or humanized antibodies that specifically bind to amino acid sequences of $(Na^+ + K^+)$-ATPase enzyme and modulate the activity of the enzyme, for treating patients suffering from or susceptible to heart disease and/or muscle contractile disorders. These antibodies are also used to block other molecules from binding to drug-interaction sites so that a patient suffering from heart disorders such as, for example, arhythmia, tachyrhithmia and the like, are useful in regulating cardiac contraction. The antibodies in this case would also function to eliminate of certain precipitating drugs, including negative inotropic agents (e.g., certain calcium channel blockers and antiarrhythmic drugs like disopyramide), cardiotoxins (e.g., amphetamines) and plasma volume expanders (e.g., nonsteroidal antiinflammatory agents and glucocorticoids).

In another preferred embodiment, the invention provides for a method of generating antibodies, wherein binding of the antibodies to an epitope of the α-subunit of $(Na^+ + K^+)$-ATPase exerts a positive inotropic effect in cardiac myocytes, comprising:
generating amino acid sequences corresponding to overlapping peptide fragments, and variants thereof, of the α-subunit of $(Na^+ + K^+)$-ATPase; and,
obtaining antibodies specific for each peptide fragment by standard methods; and,
determining the effects of the antibodies on intracellular diastolic and systolic calcium levels and cell shortenings as compared to controls.

The antibodies produced by this method, when they bind to their antigenic sites in the α-subunit of $(Na^+ + K^+)$-ATPase exert a positive inotropic effect in cardiac myocytes. The antibodies can be from antisera, polyclonal antibodies, monoclonal antibodies, and/or humanized antibodies. These antibodies are also used in immunoassays (e.g. RIA, ELISA, etc.) for diagnosing different heart and contractile disorders.

In another preferred embodiment, the invention provides for a method for diagnosing heart failure and/or contractile disorders comprising:
isolating heart tissue using standard methods; and,
obtaining cell cultures from the heart tissue using standard methods; and,
allowing the binding of inotropic antibodies to specific epitopes; and,
measuring intracellular diastolic and systolic calcium and cell shortenings.

Preferably, the molecules of the invention are administered to a patient in an effective therapeutic amount to treat the patient suffering from or susceptible to heart disease and/or muscle contractile disorders.

In another preferred embodiment, the antibodies are administered to a patient in a therapeutically effective amount to block other molecules from binding to drug-interaction sites of $(Na^+ + K^+)$-ATPase, wherein the patient is suffering from or susceptible to arhythmias, tachyrhithmias and the like.

The invention also provides for identifying molecules which target and block the KRQPRNPKTDKLVNE (SEQ ID NO: 1) or VPAISLAYEQAESD (SEQ ID NO: 2) sites of α-subunit of the $(Na^+ + K^+)$-ATPase, comprising:
contacting a myocyte with a desired molecule; and,
measuring the intracellular diastolic and systolic $Ca^{2+}$; and,
measuring cell shortening and heart function; whereby,
identifying molecules useful for therapy of patients suffering from or susceptible to heart disease and other contractile disorders.

Such molecules are used to generate inotropic antibodies and/or generate peptide-based vaccines as therapeutic agents in patients suffering from and/or susceptible to heart disease and other contractile disorders.

Other aspects of the invention are described infra.

BRIEF DESCRIPTION OF FIGURES

FIG. 2A shows the simultaneous recordings of confocal linescan images (top), intracellular $Ca^{2+}$ transients (middle), and cell shortening (bottom) in the absence (control) and presence of Jianye (20 nM for 15 min). Note that Jianye markedly increases cell contraction amplitude under a constant beating rate, accompanying an elevation of both diastolic and systolic $[Ca^{2+}]_i$.

FIG. 2B shows simultaneous recordings as in FIG. 2A, except that Jianye was mixed with the specific peptide blocker (PB95, 20 μM) prior to administration to the cell. The peptide blocker largely impeded the Jianye effects on $[Ca^{2+}]$; and contraction.

FIG. 2C is a graph showing the dose-dependent contractile response of Jianye in rat ventricular myocytes. The sigmoid dose-response curve of Jianye fits the equation $R=1+(R_{max}-1)/[1+(EC_{50}/C)^h]$, where R is the contractile response expressed in percentage of control, $R_{max}$ is the maximal contractile response, C is the Jainye concentration, $EC_{50}$ is the C at the half maximal contractile response, and h is the Hill coefficient. Curve fitting yielded the parameters $R_{max}$=396%, h=2.55 and $EC_{50}$=11.4 nM. n=4-6 for each data point.

FIG. 3A is a graph showing the effect of Jianye and ouabain on digitalis-resistant rat $(Na^++K^+)$-ATPase (100 nM).

FIG. 3B is a graph showing the effect of Jianye and ouabain on digitalis-sensitive dog $Na^+/K^+$-ATPase (16 nM).

FIG. 4A is a Western blot showing the binding of Jianye antibody to $(Na^++K^+)$-ATPase.

FIG. 4B is a Western blot showing that the Jianye antibody does not bind to $Ca^{2+}$-ATPase.

Figure 1:
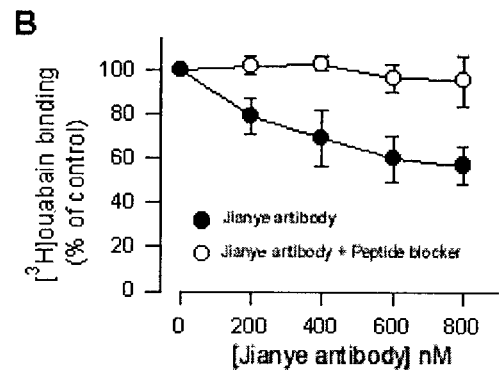
FIG. 1A is a schematic illustration showing the amino-acid composition of the Jianye antibody binding region on the $(Na^+ + K^+)$-ATPase. The primary amino acid sequence of Jianye binding site is compared among αI types from rat (SEQ ID NO:3), human (SEQ ID NO: 4), dog (SEQ ID NO: 5), pig (SEQ ID NO: 6), chicken (SEQ ID NO: 7), and αII (rat-SEQ ID NO: 8; human-SEQ ID NO: 9) and αIII (rat-SEQ ID NO: 10; human-SEQ ID NO: 11) types from rat and human isoforms of $(Na^+ + K^+)$-ATPase.
FIG. 1B is a graph which shows that site-specific antipeptide antibody displaces [$^3$H]ouabain binding on the $(Na^+ + K^+)$-ATPase. Jianye displaces [$^3$H]ouabain labeling to cardiac $(Na^+ + K^+)$-ATPase in a dose-dependent manner. Isolated rat cardiac right-side-out SL vesicles were labeled with [$^3$H] ouabain (0.13 μM) in the presence of Jianye. Filled circles: with various concentrations of Jianye as indicated in the figure. Open circles: in the presence of both Jianye and PB95 (1:500). The data represent a mean of five experiments.

DETAILED DESCRIPTION OF THE INVENTION $(Na^++K^+)$-ATPase regulates both excitability and contractility of the heart. Little is known about the molecular basis of the enzyme that underlies its cardiac regulatory functions. Here we demonstrate that the KRQPRNPKTDKLVNE (SEQ ID NO: 1) and VPAISLAYEQAESD (SEQ ID NO: 2) region, which reside in the α-subunit of rat $(Na^++K^+)$-ATPase, directly participate in the regulation of cardiac contraction. Site-specific antibodies against these peptide sequences markedly increased intracellular $Ca^{2+}$ transients and contraction in intact rat heart cells. These novel findings establish the first link between a precise structural region of the $(Na^++K^+)$-ATPase and cardiac positive inotropy.

In a preferred embodiment, the invention provides for antisera, polyclonal and monoclonal antibodies and/or humanized antibodies that specifically bind to amino acid sequences of $(Na^++K^+)$-ATPase, resulting in increased intracellular $Ca^{2+}$ transients and contraction in intact mammalian heart cells.

In accordance with the invention, it is preferred that the antibodies specifically bind to peptides having an amino acid sequence KRQPRNPKTDKLVNE (SEQ ID NO: 1) (the antibody is referred to herein as the "Jianye" antibody) and VPAISLAYEQAESD (SEQ ID NO: 2) (the antibody is referred to herein as the "Zulan" antibody).

In a preferred embodiment, the invention provides for the therapeutic use of antisera, polyclonal and monoclonal antibodies and/or humanized antibodies that specifically bind to amino acid sequences of $(Na^++K^+)$-ATPase enzyme and modulate the activity of the enzyme, for treating patients suffering from or susceptible to heart disease and/or muscle contractile disorders. These antibodies are also used to block other molecules from binding to drug-interaction sites so that a patient suffering from heart disorders such as, for example, arhythmia, tachyrhithmia and the like, are useful in regulating cardiac contraction. The antibodies in this case would also function to eliminate of certain precipitating drugs, including negative inotropic agents (e.g., certain calcium channel blockers and antiarrhythmic drugs like disopyramide), cardiotoxins (e.g., amphetamines) and plasma volume expanders (e.g., nonsteroidal antiinflammatory agents and glucocorticoids).

In another preferred embodiment, antibodies that bind to specific sequences of $(Na^++K^+)$-ATPase and can produce cardiac positive inotropy are administered to patients in need of such therapy.

In another embodiment, the molecules of the invention are used as diagnostic agents for heart disease or other contractile disorders, by detecting, in standard assays, such as ELISAs, RIAs and the like, peptides which are indicative of contractile disorders.

In another preferred embodiment, the invention provides for pharmaceutical compositions comprising peptides which are administered to patients resulting in the generation of antibodies which recognize such peptides resulting in the in vivo generation of inotropic antibodies. Particularly preferred peptides include, but are not limited to peptides with amino acid sequences KRQPRNPKTDKLVNE (SEQ ID NO: 1) and/or VPAISLAYEQAESD (SEQ ID NO: 2).

In another preferred embodiment, the invention provides for a vaccine which codes for amino acids which generate inotropic antibodies when administered in vivo to a patient in need of such therapy or treatment.

The term "treatment" or grammatical equivalents encompasses the improvement and/or reversal of the symptoms of heart failure (i.e, the ability of the heart to pump blood). "Improvement in the physiologic function" of the heart can be assessed using any of the measurements described herein (e.g., measurement of ejection fraction, fractional shortening, left ventricular internal dimension, heart rate, etc. in response to isoproterenol and/or norepinephrine), as well as any effect upon the patient's survival. A compound which causes an improvement in any parameter associated with heart failure when used in the screening methods of the instant invention may thereby be identified as a therapeutic compound.

The term "individual" as used herein refers to vertebrates, particularly members of the mammalian species and includes but is not limited to, domestic animals, sports animals, primates and humans; more particularly, the term refers to humans.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

As used herein, "contractile disorders" refers to the abnormal contractile response of muscle cells as compared to normal muscle cells. Examples of such disorders are arhythmia, tachyrhithmia, and the like.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

"Recombinant," as applied to a polynucleotide, means that the polynucleotide is the product of various combinations of cloning, restriction and/or ligation steps, and other procedures that result in a construct that is distinct from a polynucleotide found in nature.

A "gene" refers to a polynucleotide or portion of a polynucleotide comprising a sequence that encodes a protein. For most situations, it is desirable for the gene to also comprise a promoter operably linked to the coding sequence in order to effectively promote transcription. Enhancers, repressors and other regulatory sequences may also be included in order to modulate activity of the gene, as is well known in the art. (See, e.g., the references cited below).

The terms "polypeptide," "peptide," and "protein" are used interchangeably to refer to polymers of amino acids of any length. These terms also include proteins that are post-translationally modified through reactions that include glycosylation, acetylation and phosphorylation.

The terms "variant" and "amino acid sequence variant" are used interchangeably and designate polypeptides in which one or more amino acids are added and/or substituted and/or deleted and/or inserted at the N- or C-terminus or anywhere within the corresponding native sequence. In various embodiments, a "variant" polypeptide usually has at least about 75% amino acid sequence identity, or at least about 80% amino acid sequence identity, preferably at least about 85% amino acid sequence identity, even more preferably at least about 90% amino acid sequence identity, and most preferably at least about 95% amino acid sequence identity with the amino acid sequence of the corresponding native sequence polypeptide.

An "effective amount" is an amount sufficient to effect beneficial or desired clinical results. An effective amount can be administered in one or more administrations. The antibodies, peptides or vectors used as vaccines of the present invention can be administered to a patient at therapeutically effective doses to treat (including prevention) heart disease and/or other muscular contractile disorders. A therapeutically effective dose refers to that amount of the compound sufficient to result in desired treatment.

As used herein, the term "fragment or segment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and even more preferably at least about 60 to 80 or more contiguous amino acids in length. "Overlapping fragments" as used herein, refer to contiguous peptide fragments which begin at the amino terminal end of a protein and end at the carboxy terminal end of the protein. Each peptide fragment has at least about one contiguous amino acid position in common with the next peptide fragment, more preferably at least about three contiguous amino acid positions in common, most preferably at least about ten contiguous amino acid positions in common.

As used herein, the term "substantially pure" describes a compound (e.g., a protein or polypeptide) which has been separated from components which naturally accompany it. Typically, a compound is substantially pure when at least 10%, more preferably at least 20%, more preferably at least 50%, more preferably at least 60%, more preferably at least 75%, more preferably at least 90%, and even more preferably at least 99%, of the total material (by volume, by wet or dry weight, or by mole percent or mole fraction) in a sample is the compound of interest. Purity can be measured by any appropriate method. In the case of polypeptides, for example, purity can be measured by column chromatography, polyacrylamide gel electrophoresis, or HPLC analysis. A compound such as a protein is also substantially purified when it is essentially free of naturally associated components or when it is separated from the native contaminants which accompany it in its natural state.

A "heterologous" component refers to a component that is introduced into or produced within a different entity from that in which it is naturally located. For example, a polynucleotide derived from one organism and introduced by genetic engineering techniques into a different organism is a heterologous polynucleotide which, if expressed, can encode a heterologous polypeptide. Similarly, a promoter or enhancer that is removed from its native coding sequence and operably linked to a different coding sequence is a heterologous promoter or enhancer.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment such as the sequences adjacent to the fragment in a genome in which it naturally occurs. The term also applies to nucleic acids which have been substantially purified from other components which naturally accompany the nucleic acid, e.g., RNA or DNA, which has been purified from proteins which naturally accompany it in the cell.

"Homologous", as used herein, refers to the subunit sequence similarity between two polymeric molecules, e.g., between two nucleic acid molecules such as two DNA molecules, or two polypeptide molecules. When a subunit position in both of the two molecules is occupied by the same monomeric subunit (e.g., if a position in each of two DNA molecules is occupied by adenine) then they are homologous at that position. The homology between two sequences is a direct function of the number of matching or homologous positions. For example, if 5 of 10 positions in two compound sequences are matched or homologous then the two sequences are 50% homologous, if 9 of 10 are matched or homologous, the two sequences share 90% homology. By way of example, the DNA sequences 3' ATTGCC 5' and 3' TTTCCG 5' share 50% homology.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. "Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

A "replicon" refers to a polynucleotide comprising an origin of replication which allows for replication of the polynucleotide in an appropriate host cell. Examples include replicons of a target cell into which a heterologous nucleic acid might be integrated (e.g., nuclear and mitochondrial chromosomes), as well as extrachromosomal replicons (such as replicating plasmids and episomes).

In accordance with the invention, the antibodies of the invention are also used as diagnostic agents which detect muscle contractile disorders, especially, for example, in the heart. In one embodiment, any of the above-described molecules can be labeled, either detectably, as with a radioisotope, a paramagnetic atom, a fluorescent moiety, an enzyme, etc. in order to facilitate its detection in, for example, in situ or in vivo assays. The molecules may be labeled with reagents such as biotin, in order to, for example, facilitate their recovery, and/or detection.

As used herein, "inotropic agents" or "inotropic antibodies" will be used interchangeably and refers to the effect such agents produce, i.e. improves cardiac output by increasing the force of myocardial muscle contraction. "Positive inotropic effect" means that the contractility of the cells is enhanced in a dose-dependent manner. A positive inotropic effect-producing amount of antibodies or peptides of the invention can be administered to a "mammalian host" (e.g., a human) to treat cardiac malfunction (e.g., congestive heart failure, paroxysmal atrial tachycardia, atrial fibrillation and flutter). Administration can be either enteral (i.e., oral) or parenteral (e.g., via intravenous, subcutaneous or intramuscular injection).

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495-497, 1975, and U.S. Pat. No. 4,376,110.

As used herein, an "antigenic determinant" is the portion of an antigen molecule that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. *Proc. Natl. Acad. Sci.* U.S.A. 81:3998-4002; PCT Publication No. WO 84/03564; and PCT Publication No. WO 84/03506.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Immunoassay" is an assay that uses an antibody to specifically bind an antigen (e.g., a marker). The immunoassay is characterized by the use of specific binding properties of a particular antibody to isolate, target, and/or quantify the antigen.

In another preferred embodiment, where the antibodies or their fragments are intended for therapeutic purposes, it is desirable to "humanize" them in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., International Patent Publication PCT/U.S.86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041-1043 (1988); Liu, A. Y. et al. *Proc. Natl. Acad. Sci.* USA 84:3439-3443 (1987); Liu, A.Y. et al., *J. Immunol.* 139:3521-3526 (1987); Sun, L. K. et al., *Proc. Natl. Acad. Sci.* USA 84:214-218 (1987); Nishimura, Y. et al., *Canc. Res.* 47:999-1005 (1987); Wood, C. R. et al., *Nature* 314:446-449 (1985)); Shaw et al., *J. Natl. Cancer Inst.* 80:1553-1559 (1988); all of which references are incorporated herein by reference). General reviews of "humanized" chimeric antibodies are provided by Morrison, S. L. (*Science,* 229:1202-1207 (1985)) and by Oi, V. T. et al., *BioTechniques* 4:214 (1986); which references are incorporated herein by reference).

Suitable "humanized" antibodies can alternatively be produced by CDR or CEA substitution (Jones, P. T. et al., *Nature* 321:552-525 (1986); Verhoeyan et al., *Science* 239:1534 (1988); Beidler, C. B. et al., *J. Immunol.* 141:4053-4060 (1988); all of which references are incorporated herein by reference).

As used herein, the term "humanized" antibody refers to a molecule that has its CDRs (complementarily determining regions) derived from a non-human species immunoglobulin and the remainder of the antibody molecule derived mainly from a human immunoglobulin. The term "antibody" as used herein, unless indicated otherwise, is used broadly to refer to both antibody molecules and a variety of antibody derived molecules. Such antibody derived molecules comprise at least one variable region (either a heavy chain of light chain variable region) and include molecules such as Fab fragments, Fab' fragments, F(ab')$_2$ fragments, Fd fragments, Fab' fragments, Fd fragments, Fabc fragments, Sc antibodies (single chain antibodies), diabodies, individual antibody light chains, individual antibody heavy chains, chimeric fusions between antibody chains and other molecules, and the like.

The term "variable region" as used herein in reference to immunoglobulin molecules has the ordinary meaning given to the term by the person of ordinary skill in the act of immunology. Both antibody heavy chains and antibody light chains may be divided into a "variable region" and a "constant region". The point of division between a variable region and a heavy region may readily be determined by the person of ordinary skill in the art by reference to standard texts describing antibody structure, e.g., Kabat et al "Sequences of Proteins of Immunological Interest: 5th Edition" U.S. Department of Health and Human Services, U.S. Government Printing Office (1991).

The present invention provides humanized antibody molecules specific for peptides having an amino acid sequence KRQPRNPKTDKLVNE (SEQ ID NO: 1) and VPAISLAYEQAESD (SEQ ID NO: 2). However, the invention is not limited to these sequences but applies to any sequence in which antibodies can bind resulting in cardiac positive inotropy. In accordance with the present invention, the humanized antibodies are comprised of antigen specific regions in which at least parts of the CDRs of the heavy and/or light chain variable regions of a human antibody (the receptor antibody) have been substituted by analogous parts of CDRs of a murine monoclonal antibody and the humanized antibody can specifically bind to the same as the Jianye or Zulan antibodies. In a preferred embodiment of the subject invention, the CDR regions of the humanized Jianye or Zulan antibodies are derived from rabbits as described in the examples which follow. Some of the humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitutions that improve the binding properties of a humanized antibody region that is specific for the same target as the Jianye and Zulan antibodies. A minimal number of substitutions are made to the framework region in order to avoid large-scale introductions of non-human framework residues and to ensure minimal immunogenicity of the humanized antibody in humans. The donor monoclonal antibodies of the present invention Jianye and Zulan antibodies, which are specific for the rat α-subunit of $(Na^+ + K^+)$-ATPase i.e., KRQPRNPKTDKLVNE (SEQ ID NO: 1) and VPAISLAYEQAESD (SEQ ID NO: 2) peptides respectively.

The humanized antibodies compositions of the invention or other therapeutic agents of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, Remington's Pharmaceutical Science, 15th Ed., Mack Publishing Company, Easton, Pa. (1980), which is incorporated herein by reference.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon-the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography. A typical daily dose for the therapeutic molecules of the invention (i.e., antibodies, peptides, vectors encoding peptides) of the present invention might range from about 1 μg/kg to about 100 mg/kg of patient body weight or more per day, depending on the factors mentioned above, preferably about 10 μg/kg/day to 10 mg/kg/day.

Pharmaceutical compositions for use in accordance with the present invention can be formulated in conventional manner using one or more physiologically acceptable carriers or excipients. Thus, the compounds and their physiologically acceptable salts and solvates can be formulated for administration by intra venous or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate. talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

The treatment can be monitored by various ways, including echography and electrocardiograms. "Electrocardiogram" refers to a graphic tracing of variations in electrical potential caused by the excitation of the heart muscle which may be detected at the body surface. "Electrocardiogram" may be abbreviated as "ECG" or "EKG". The signals may be detected by means of metal electrodes attached to the extremities and chest wall, and may then be amplified by a sensitive voltmeter such as the electrocardiograph. The ECG waveforms are generally labeled alphabetically beginning with the P wave, which represents atrial depolarization. Approximately 0.16 seconds after the onset of the P wave, the QRS waves generally appear as a result of depolarization of the ventricular muscle, which initiates contraction of the ventricles. Finally, the T wave results from repolarization of the ventricles, which represents the onset of ventricular relaxation. The duration of the "T" wave cycle time is that time in a heart cycle when it is most vulnerable to fibrillation, a condition where the cardiac muscle fiber contracts asynchronously. Electrocardiography is further described in Harrison's Principles of Internal Medicine, Thirteenth Ed., McGraw-Hill, Inc., Chapter 189, pp. 954-966 (1994), the disclosures of which are hereby incorporated herein by reference, in their entirety.

Echocardiography is the preferred method of monitoring treatment using the molecules of the invention. "Echocardiography" (Echo) uses sound waves to form a picture of the heart valves and heart muscle. The Echo machine sends sound waves to a transducer (a sound sensitive instrument) that is placed on the patient's chest. The sound waves are reflected by the heart walls (muscle) and heart valves, back to the transducer, which changes the sound into a picture. There is no special preparation for this test. Gel is applied on the patient's chest and a transducer is placed over the heart area. Heart structures are examined by changing the direction of the transducer. The sound waves cause no discomfort. When the test is completed the gel is wiped off easily. Thus, an Echo detects the changes and provides information about heart chamber size, wall motion, valve movements, and structural changes in and around the heart.

The invention also provides for vectors which are used for treating a patient suffering from or susceptible heart disease. As used herein, a "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available (see, e.g., the various references cited below).

As used herein, the term "administering a molecule to a cell" (e.g., an expression vector, nucleic acid, peptide, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

A "recombinant viral vector" refers to a viral vector comprising one or more heterologous genes or sequences. Since many viral vectors exhibit size-constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation) (see, e.g., the references and illustrations below). Modified viral vectors in which a polynucleotide to be delivered is carried on the outside of the viral particle have also been described (see, e.g., Curiel, D T, et al. *PNAS* 88: 8850-8854, 1991).

Viral "packaging" as used herein refers to a series of intracellular events that results in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" genes, found in many viral genomes, are genes encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain genes encoding the missing functions which can be supplied in trans). For example, such packaging genes can be stably integrated into a replicon of the packaging cell line or they can be introduced by transfection with a "packaging plasmid" or helper virus carrying genes encoding the missing functions.

A "detectable marker gene" is a gene that allows cells carrying the gene to be specifically detected (e.g., distinguished from cells which do not carry the marker gene). A large variety of such marker genes are known in the art. Preferred examples thereof include detectable marker genes which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining, as described below.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., WO 92/08796, published May 29, 1992, and WO 94/28143, published Dec. 8, 1994). Such marker genes can provide an added measure of control that can be advantageous in gene therapy contexts. "Treatment" or "therapy" as used herein also refers to administering, to an individual patient, agents that are capable of eliciting a prophylactic, curative or other beneficial effect in the individual.

"Gene therapy" as used herein refers to administering, to an individual patient, vectors comprising a therapeutic gene.

A "therapeutic polynucleotide" or "therapeutic gene" refers to a nucleotide sequence that is capable, when transferred to an individual, of eliciting a prophylactic, curative or other beneficial effect in the individual.

The practice of the present invention can suitably employ, unless otherwise indicated, conventional techniques of molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W. B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

Preferred vectors for use in the present invention include viral vectors, lipid-based vectors and other vectors that are capable of delivering DNA to non-dividing cells in vivo. Presently preferred are viral vectors, particularly replication-defective viral vectors (including, for example replication-defective adenovirus vectors and adeno-associated virus (AAV) vectors. For ease of production and use in the present invention, replication-defective adenovirus vectors are presently most preferred.

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein. Targeted vectors include vectors (such as viruses, non-viral protein-based vectors and lipid-based vectors) in which delivery results in transgene expression that is relatively limited to particular host cells or host cell types. By way of illustration, therapeutic molecules, for example, nucleic acid sequences encoding for the peptides of the invention, to be delivered to a patient can be operably linked to heterologous tissue-specific promoters thereby restricting expression to cells in that particular tissue.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The presently preferred means of in vivo delivery, is by injection of the vector into a blood vessel directly supplying the myocardium, preferably by injection into a coronary artery. Such injection is preferably achieved by catheter introduced substantially (typically at least about 1 cm) within the ostium of one or both coronary arteries or one or more saphenous veins or internal mammary artery grafts or other conduits delivering blood to the myocardium.

By injecting the vector stock, preferably containing no wild-type virus, deeply into the lumen of one or both coronary arteries (or grafts and other vascular conduits), preferably into both the right and left coronary arteries (or grafts and other vascular conduits), and preferably in an amount of about $10^7$-$10^{13}$ viral particles as determined by optical densitometry (more preferably $10^9$-$10^{11}$ viral particles), it is possible to locally transfect a desired number of cells, especially cardiac myocytes, with genes that encode proteins that regulate cardiac contraction, such as, for example, the peptides discussed infra, thereby maximizing therapeutic efficacy of gene transfer, and minimizing undesirable effects at extracardiac sites and the possibility of an inflammatory response to viral proteins. Vector constructs that are specifically targeted to the myocardium, such as vectors incorporating myocardial-specific binding or uptake components, and/or which incorporate inotropic molecules, for example, the peptides described above, that are under the control of myocardial-specific transcriptional regulatory sequences (e.g., ventricular myocyte-specific promoters) can be used in place of or, preferably, in addition to such directed injection techniques as a means of further restricting expression to the myocardium, especially the ventricular myocytes. For vectors that can elicit an immune response, it is preferable to inject the vector directly into a blood vessel supplying the myocardium as described above, although the additional techniques for restricting the potential for extracardiac expression can also be employed. Additional references describing cell types found in the blood vessels, and the structure of the vasculature which may be useful in the methods of the present invention include the following: W. Bloom & D. Fawcett, A Textbook of Histology, 10th Ed., (W. B. Saunders Co. 1975). Methods of uses of gene transfer for the treatment or prevention of disease, including heart disease are described, e.g., Methods in Molecular Biology, Vol. 7: Gene Transfer and Expression Protocols, Murray, E. (ed.), Humana Press, Clifton, N.J. (1991); Mazur et al., Molecular and Cellular Pharmacology, 21:104-111, 1994; French, Herz 18:222-229, 1993; Williams, American Journal of Medical Sciences 306:129-136, 1993; and Schneider and French, Circulation 88:1937-1942, 1993.

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The invention also provides for methods for identifying peptides and antibodies which are positive inotropic agents. To prepare an antibody that specifically binds to a region of the $Na^+$, $K^+$- ATPase, purified peptides or their nucleic acid sequences representing the different subunits of $Na^+$, $K^+$- ATPase can be used. Using the purified peptides or their nucleic acid sequences representing the different subunits of $Na^+$, $K^+$-ATPase, antibodies that specifically bind to a desired peptide can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256: 495-497 (1975). Such techniques include, but are not limited to, antibody preparation by selection of antibodies from libraries of recombinant antibodies in phage or similar vectors, as well as preparation of polyclonal and monoclonal antibodies by immunizing animals (see, e.g., Huse et al, *Science* 246:1275-1281 (1989); Ward et al., *Nature* 341:544-546 (1989)); humanized antibodies; production of antibodies by any of the methods discussed above. After the antibody is provided, the specificity of the antibody can be detected using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra.

To determine whether these identified antibodies are positive inotropic agents, standard assays such as those described in the Examples which follow can be used. For example, measurement of cell contraction assays; confocal $Ca^{2+}$ imaging; $Na^+$, $K^+$- ATPase activity assays and the like.

The following non-limiting examples are illustrative. All documents mentioned herein are hereby incorporated by reference.

EXAMPLES

In the following examples, the following materials and methods were employed.

Materials And Methods

Materials.

All reagents were purchased from Sigma Chemical Co., unless specified. [21,22-$^3$H]ouabain (15-50 Ci/mM) was from Amersham Pharmacia Biotech. Highly purified dog kidney ($Na^+$+$K^+$)-ATPase was a gift from Dr. Jack Kyte.

Antibody Preparation.

The KRQPRNPKTDKLVNE and VPAISLAYEQAESD peptides were synthesized according to the protein sequence reported (Schneider, J. W., Mercer, R. W., Caplan, M., Emanuel, J. R., Sweadner, K. J., Benz, E. J., Levenson, R. (1985) *Proc. Natl. Acad. Sci. U.S.A.* 82, 6357-6361; Xie, Z., Li, H., Liu, G., Wang, Y., Askari, A., Mercer, R. W. (1994) Cloning of the dog Na/K-ATPase alpha 1 subunit. *The Na Pump*. (Bamberg, S., and Schoner, W., Eds), pp. 49-52, Springer-Verlag, New York, N.Y.; Shull, M. M., Lingrel, J. B. (1987) *Proc. Natl. Acad. Sci. U.S.A.* 84, 4039-4043). The polyclonal Jianye antibody was generated in New Zealand White rabbits using KLH as a peptide carrier (Genemed). The immunoglobulins (IgG) were purified through an affinity column directed against the same synthetic peptide of the ($Na^+$+$K^+$)-ATPase. Purified Jianye recognizes both denatured (by Western blots) and native ($Na^+$+$K^+$)-ATPase (by immunocytostaining). Synthetic peptide was also utilized as the specific peptide blockers for the antibodies.

Isolation of Cardiac Myocytes:

Ventricular cardiac myocytes were isolated from adult Sprague-Dawley rats (2-3 months old; weight 225-300 g) using standard enzymatic techniques. Briefly, following anesthesia (sodium pentobarbital, 100 mg/kg), the heart was quickly removed from the chest and aortic perfused at constant pressure (100 cmH$_2$O) at 37° C. for 3 minutes with a $Ca^{2+}$-free bicarbonate-based buffer containing 120 mM NaCl, 5.4 mM MgSO$_4$, 1.2 mM NaH$_2$PO$_4$, 5.6 mM glucose, 20mM NaHCO$_3$, and 5 mM taurine, in the presence of O$_2$ (95%)-CO$_2$ (5%). The enzymatic digestion was initiated by adding collagenase (Worthington Type II, 1 mg/ml) to the perfusion solution. Calcium (50 µM) was added to the enzyme solution when the heart became swollen. About 7 minutes later, the left ventricle was quickly removed, cut into several pieces, and further digested on a shaker (60-70 rpm) for 10 minutes in the same enzyme solution. The supernatant containing the dispersed myocytes was filtered into a test tube and gently centrifuged at 500 rpm for 1 minute. The cell pellet was then promptly resuspended in a solution containing 0.125 M $Ca^{2+}$. The supernatant was aspirated after the myocytes were pelleted by gravity for 10 minutes and the myocytes were then resuspended in a solution containing 0.25 mM $Ca^{2+}$. The shake-harvest procedure was repeated several times until all of the pieces were digested. For freshly isolated cells, myocytes were suspended in HEPES-buffer consisting of 1 mM $CaCl_2$, 0.137 mM NaCl, 5.4 mM KCl, 15 mM dextrose, 1.3 mM $MgSO_4$, 1.2 mM $NaH_2PO4$, and 20 mM HEPES, pH7.4.

Measurement of Cell Contraction (Cell Shortening):

Myocytes were placed on an inverted microscope (Zeiss model IM-35), superfused with HEPES-buffered solution at a flow rate of 1.8 ml/min, and electrically stimulated at 0.5 Hz at 23° C. Cell length was monitored from the bright field image (650 nm to 750 nm red light illumination) by an optical edge-tracking method using a photodiode array (model 1024 SAQ, Reticon) with a 3 ms time resolution. The contraction amplitude was measured as the percentage of shortening of cell length.

Confocal Imaging of $Ca^{2+}$ Transients and Cell Morphology:

Myocytes were placed on the stage of a Zeiss LSM-410 on an inverted confocal microscope (Carl Zeiss) and excited by the 488 nm line of an argon laser. Intracellular loading of the $Ca^{2+}$ indicator fluo-4 was achieved by a 10 minute incubation of the myocytes in HEPES buffer containing 10 µM fluo-4 (Molecular Probes), followed by a 15 min wash. All images were taken in the line scan mode (2 ms/line, 0.1-0.3 µm/pixel), with the scan line oriented along the long axis of the myocytes, avoiding the nuclei of the cell. The microscope was equipped with a Zeiss Plan-Neofluar 40X, NA 1.3, oil-immersion objective, with an axial resolution of 1.1µm. IDL software (Research Systems, Boulder Co.) was used for the image processing, data analysis, and presentations.

Confocal $Ca^{2+}$ Imaging.

Intracellular loading of the $Ca^{2+}$ indicator fluo-4 was achieved by a 10-min incubation of the myocytes with 10 µM fluo-4 AM (Molecular Probes). Confocal linescan images of intracellular $Ca^{2+}$ and cell length were acquired using a Zeiss LSM410 confocal microscope (Carl Zeiss) equipped with an argon laser (488 nm) and a Plan-Neofluar 40X, NA 1.3, oil-immersion objective. The scan line was oriented along the long axis of the myocyte, avoiding nuclei of the cells; the scan rate and spatial resolutions were 2.0 ms/line, and 0.4×0.4×1.0 (xyz) $\mu m^3$, respectively. IDL software (Research Systems, Boulder Co.) was used for image processing, data analysis, and presentation. $Ca^{2+}$ transients were calculated using the formula: $[Ca^{2+}]=k_d R/\{(k_d/[Ca^{2+}]_{rest}+1)-R\}$, where $R=F/F_0$, the resting $Ca^{2+}$ concentration $[Ca^{2+}]_{rest}=100$ nM, and the dissociation constant $k_d=1.1$ µM.

Isolation of Sarcolemmal Vesicles and Purification of $(Na^+ + K^+)$-ATPase:

Rat cardiac sarcolemmal (SL) vesicles were isolated from rat heart muscle by sucrose flotation method. The vesicles were tested with saponin and were predominately right-side-out in orientation. $(Na^+ + K^+)$-ATPase was purified as described previously (Kyte, J. (1971) *Biochemistry*, 246: 4157-4165). Briefly, the SL vesicles (4.4 mg/ml) were titrated with 0.58 mg/ml of SDS in the presence of 2 mM ATP at 20° C. for 30 min. The SDS titrated fractions were then loaded on the top of a sucrose (W/W) step gradient constructed with 10 ml of 37.3% (bottom step), 20 ml of 28.8%, and 10 ml of 15% in a Ti 60 tube, and centrifuged at 40,000 rpm for 90 min. The fractions that contain $(Na^+ + K^+)$-ATPase (between 37.3 and 28.8% on the sucrose gradient) were carefully collected and sedimented at 40,000 rpm for 60 minutes. The purified enzyme was resuspended in a sucrose (250 mM)/histidinium chloride (30 mM) buffer, pH 7.2, quick-frozen in liquid nitrogen and stored at −70° C. Highly purified dog kidney $(Na^+ + K^+)$-ATPase was a gift from Dr. Jack Kyte.

Determination of $(Na^+ + K^+)$-ATPase Activity:

The enzymatic activity was determined as described previously (Kyte J., et al., (1987) *Biochemistry*, 26:8350-8360) with modifications. Briefly, purified rat or dog $(Na^+ + K^+)$-ATPase was incubated with or without Jianye or ouabain in the presence of 100 mM $Na^+$ for 30 min at room temperature. The reaction was initiated by adding 3 mM MgATP and 20 mM $K^+$ in a final volume of 0.25 ml at 37° C. for 30 min and terminated by adding 0.75 ml quench solution and 0.025 ml developer. The color was allowed to develop for 30 min at room temperature and the concentration of phosphate was then determined at 700 nm using a spectrophotometer.

[$^3$H]ouabain Binding:

Cardiac SL vesicles (3 mg/ml) were incubated with or without various concentrations of Jianye antibody for 30 minutes at room temperature in a medium containing 1 mM MgATP, 100 mM NaCl, and 10 mM Tris/HCl buffer (ph 7.4). [$^3$H]ouabain (60 nM) was then added to the samples for 30 minutes at 37° C. The binding reaction was stopped by pelleting the samples at 14,000 rpm for 10 minutes. The pellet was washed three times with 10 mM Tris/HCl buffer and then dissolved in 100 µl 10% SDS solution. An aliquot (20 or 50 Ml) was taken from each sample and radioactivity determined using a β-scintillation counter. The percent of [$^3$H]ouabain binding to the enzyme was then calculated.

Example 1

Jianye Antibody and its Effect on [$^3$H]Ouabain Binding

To identify potential structural determinants of the $(Na^+ + K^+)$-ATPase that mediate the positive inotropic effect on the heart, we have generated anti-peptide antibodies against the known antigenic sites on the enzyme. Among them, the Jianye polyclonal antibody was raised to specifically recognize the KRQPRNPKTDKLVNE (SEQ ID NO: 1), peptide (Schneider J.W., et al., (1985) *Proc. Natl. Acad. Sci.* USA, 82:6357-6361; Xie, Z.; et al., (1994), The Na Pump, Bamberg, S., and Schoner, W., Eds., pp. 49-52, Springer-Verlag, New York, NY; Shull, M.M., et al., *Proc. Natl. Acad. Sci.* USA (1987) 84:4038-4043) of the rat α-subunit of the $(Na^+ + K^+)$-ATPase, which is located in the extracellular domain of the enzyme. Purified antibody recognized both denatured and native $(Na^+ + K^+)$-ATPase of rat cardiac myocytes, as evidenced by Western blots and immunocytostaining, respectively. FIG. 1A shows that the amino acid sequence of this region is identical among the αI sub-units of both digitalis-resistant (e.g., rat) and -sensitive forms (e.g., dog and human) of $(Na^+ + K^+)$-ATPase, and is highly conserved among isoforms of the enzyme as well.

Example 2

The Relationship between the Binding Sites of Jianye and Cardiac Glycosides on the $Na^+/K^+$ATPase Cardiac glycosides and related drugs induce positive inotropic effect by binding to the outer cell surface of the a subunit of the $(Na^+ + K^+)$-ATPase. To investigate the relationship between the binding sites of Jianye and cardiac glycosides on the $Na^+/K^+$ATPase, [$^3$H]ouabain (0.13 µ,M) was used to react with isolated rat cardiac sarcolemmal right-side-out vesicles (2 mg/ml) with or without Jianye at various concentrations. FIG. 1B shows that Jianye antagonized [$^3$H] ouabain binding by reducing the [$^3$H]ouabain labeling by 21, 31, 40, and 43% in the presence of 0.2, 0.4, 0.6, and 0.8 µM Jianye, respectively. However, the [$^3$H]ouabain labeling was not affected when the immuno-active sites of the Jianye were saturated by a peptide blocker KRQPRNPKTDKLVNE (SEQ ID NO: 1) (PB) prior to adding [$^3$H]ouabain to the SL vesicles. These results show that Jianye acts like an antagonist of [$^3$H]ouabain (FIG. 1B) and suggest that the Jianye binding region of the enzyme may contain essential structural and functional information for cardiac glycoside binding and the ensuing biological action.

Example 3

Effect of Jianye on Cardiac Contraction and $Ca^{2+}$ Transients

Figure 2:
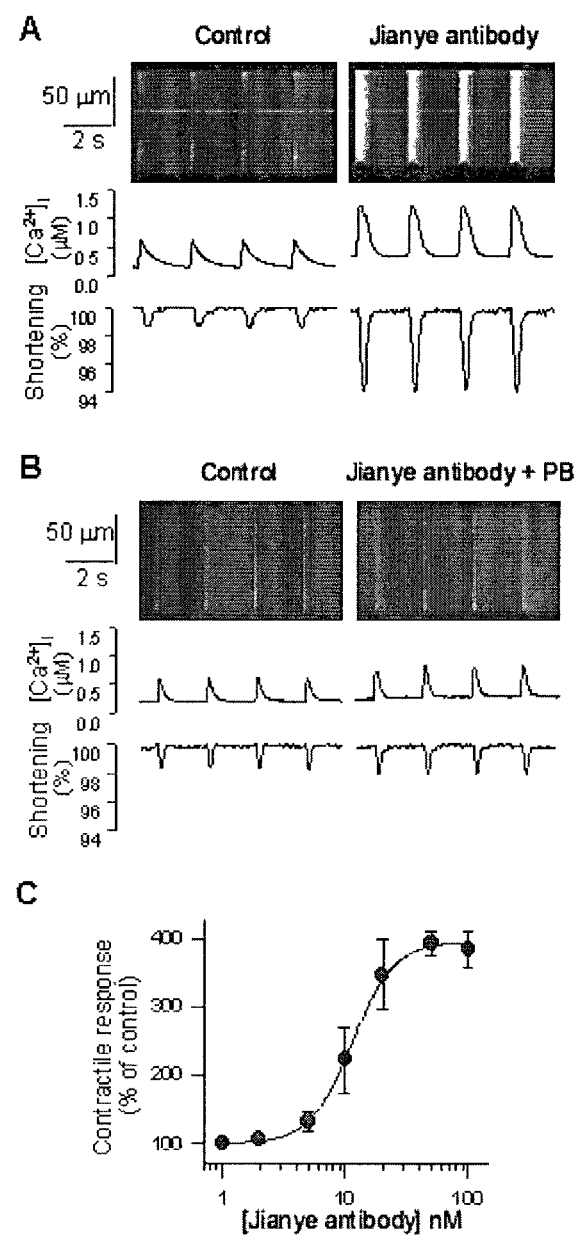
FIG. 2 shows the effects of Jianye antibody on cell contraction and intracellular $Ca^{2+}$ transients in rat heart cells.

We next determined whether the binding of Jianye to the ($Na^+$+$K^+$)-ATPase affects cardiac contractility. Confocal linescan imaging was employed in conjunction with the $Ca^{2+}$-sensitive indicator, fluo-4, to monitor simultaneously intracellular $Ca^{2+}$ transients and contraction in single rat ventricular myocytes. Cells were continuously excited by electrical stimuli and contracted at 0.5 Hz (FIG. 2). Administration of Jianye (20 nM, 10-15 min) markedly increased systolic $[Ca^{2+}]_i$ and cell shortenings to 191±24%, (n=5, P<0.01) and 347±51% (n=5, P<0.01) of controls, respectively (FIG. 2A). The diastolic $[Ca^{2+}]_i$ level was also elevated from 100 nM to 161±13 nM (n=5, P<0.01) while accompanying a reduction of the resting cell length (FIG. 2A). Hence, Jianye exerts a positive inotropic effect in cardiac myocytes via enhancement of diastolic and systolic $[Ca^{2+}]_i$. These results show that Jianye is a novel inotropic antibody and provide the first direct link between the molecular sequence and the contractile action of the ($Na^+$+$K^+$)-ATPase in heart cells.

Example 4

To Ascertain the Specificity of the binding of JIANYE to the ($Na^+$+$K^+$)-ATPase A specific peptide blocker PB(KRQPRNPKTDKLVNE) (SEQ ID NO: 1) was mixed with Jianye prior to administration to cardiac myocytes. FIG. 2B shows that this synthetic peptide acted as a Jianye blocker, and largely abolished the increases both in $Ca^{2+}$ transients and contraction. These results confirmed that the binding of Jianye to its specific antigenic site is necessary and sufficient for Jianye to alter intracellular $Ca^{2+}$ handling and to augment contractility in heart cells.

We further quantified the potency and efficacy of Jianye in modulating cell contractility in rat cardiac myocytes. FIG. 2C shows that Jianye monophasically increased the amplitude of contraction in a dose-dependent manner, with a half effective concentration ($EC_{50}$) of 11.4 nM. The dose-response curve exhibited a Hill coefficient of 2.55; the threshold and maximal contractile responses were attained at 5 and 50 nM of Jianye, respectively, with the maximum cell contraction increasing four times compared with control (FIG. 2C). These results indicate that Jianye is a powerful inotropic agent.

Example 5

Effect of Jianye on ($Na^+$+$K^+$)-ATPase Activity

Figure 3:
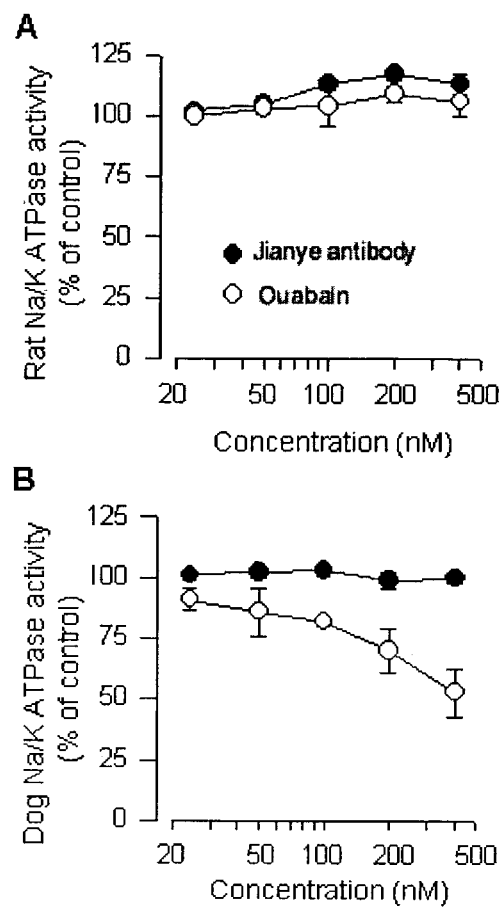
FIG. 3 shows graphs which illustrate the effect of Jianye and ouabain on $(Na^++K^+)$-ATPase activity. Filled circles: Jianye. Open circles: ouabain. Note that ouabain at the concentrations used did not inactivate ouabain-resistant rat $(Na^++K^+)$ATPase, but reduced the enzymatic activity of the ouabain-sensitive dog $(Na^++K^+)$-ATPase. Note that Jianye inactivated neither, regardless of cardiac glycoside sensitivity. The data represent a mean of four experiments.

To investigate whether the binding of Jianye affects ($Na^+$+$K^+$)-ATPase activity, we measured ($Na^+$+$K^+$)-ATPase (100 nM) activity in the presence of 100 mM $Na^+$, 20 mM $K^+$, 3 mM MgATP, and various concentrations of Jianye or ouabain. FIG. 3 shows that no inhibition of digitalis-resistant rat ($Na^+$+$K^+$)-ATPase activity was detected over the concentration range of Jianye (24-400 nM) where both $EC_{50}$, and the maximum cardiac cell contraction were reached (FIGS. 2C and 3A). To exclude the possibility that the inability of Jianye to inhibit enzymatic activity may be due to the digitalis-resistant nature of rat ($Na^+$+$K^+$)-ATPase (FIG. 3), we tested the effect of Jianye on the digitalis-sensitive ($Na^+$+$K^+$)-ATPase (16 nM) purified from dog kidney. FIG. 3B shows that ouabain, but not Jianye, inhibited the ATP hydrolysis by up to 47% in the same concentration range (24-400 nM) under the same experimental conditions. Since the Jianye concentration (400 nM) was 25-times higher than dog ($Na^+$+$K^+$)-ATPase (FIG. 3B), this further corroborates that the binding of Jianye to the ($Na^+$+$K^+$)-ATPase does not inactivate enzymatic activity. These results show that Jianye-enhanced heart cell contraction, is independent of inactivation of the ($Na^+$+$K^+$)-ATPase.

The molecular basis of the ($Na^+$+$K^+$)-ATPase that regulates excitation/contraction of the heart is not completely understood. In the present study, we have identified a structural region of the ($Na^+$+$K^+$)-ATPase that directly participates in the regulation of cardiac contractility. This was demonstrated by the binding of a site-specific antibody (Jianye) to the ($Na^+$+$K^+$)-ATPase, resulting in a marked increase of the $Ca^{2+}$ transients and contraction in rat cardiac myocytes (FIG. 2A). Moreover, experimental data show that Jianye increased heart cell contractile force in a dose-dependent fashion with an $EC_{50}$ of 11.4 nM (FIG. 2C), demonstrating that Jianye induces a positive inotropic action and that Jianye is a potent inotropic reagent. The Jianye-induced biological effects on heart cells were completely abolished by a peptide blocker (PB) (FIG. 2B), further indicating the specificity of the Jianye action.

Jianye acts from the outside of intact myocytes to increase intracellular $Ca^{2+}$ concentration and induce a positive inotropic action, supporting the concept that the KRQPRNPKTDKLVNE (SEQ ID NO: 1) epitope of the ($Na^+$+$K^+$)-ATPase is located at the extracellular side of the enzyme. Furthermore, results from the in vivo mouse heart study showed that Jianye induced a positive inotropic action on mouse heart as demonstrated in terms of intraventricular pressure-volume loops after administration of JIANYE. The results of this in vivo study further suggest that the binding site of the inotropic antibody is accessible from the membrane surface.

Figure 4:
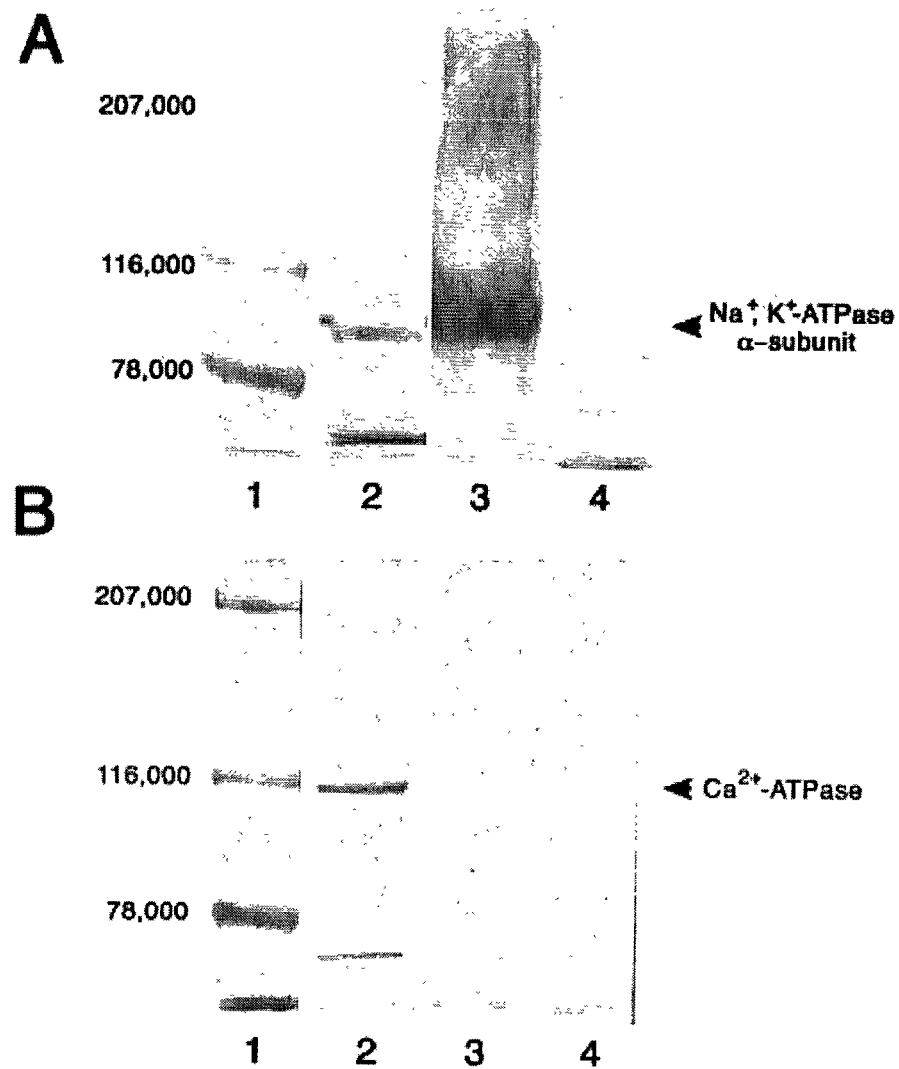
FIG. 4 are Western blots which show specific binding of Jianye to the α-polypeptide of $(Na^++K^+)$-ATPase in Western transfer analysis. Samples were dissolved by the Laemmli sample buffer (Bio-Rad) and separated by electrophoresis on a gel of 5% polyacrylamide. The separated polypeptides were then transferred to nitrocellulose membranes and reacted with Jianye directed against the sequence -KRQPRNPKTD-KLVNE (SEQ ID NO: 1) followed by goat anti-rabbit IgG (Fc) to which alkaline phosphatase (AP) was attached. The distribution of bound antibody was determined by AP-dependent staining. Lanes A1 and B1: Standard polypeptides. Lane A2: Rat heart homogenate (30 μg) with Jianye. Lane A3: Dog SL vesicles (20 μg) with Jianye. Lane A4: Rat heart homogenate with secondary antibody only. Lane B2: SR vesicles (20 μg) with SERCA2 (anti-SR $Ca^{2+}$-ATPase). Lane B3: SR vesicles with Jianye. Lane B4: SR vesicles with secondary antibody only. Jianye specifically binds to the $(Na^++K^+)$-ATPase in rat heart homogenates and dog SL vesicles, but not to both SL and SR $Ca^{2+}$-ATPases.

To examine the possibility that Jianye might bind to $Ca^{2+}$ ATPase to induce an inotropy, Western blotting was performed using the rat heart homogenate. The results show that Jianye specifically detected ($Na^+$+$K^+$)-ATPase in both rat heart homogenates (FIG. 4A, lane 2) and dog kidney vesicles (FIG. 4A, lane 3), but recognized neither sarcolemma $Ca^{2+}$-ATPase (FIG. 4A, lane 2), nor sarcoplasmic reticulum $Ca^{2+}$-ATPase (FIG. 4B). These results further substantiate that Jianye specifically binds to the ($Na^+$+$K^+$)-ATPase to induce its physiological action.

According to the reported mechanisms of digitalis-induced inotropic action, digitalis inhibits the ($Na^+$+$K^+$)-ATPase which, in turn, increases the intracellular $Na^+$ ion concentration $[Na^+]_i$. The increase in $[Na^+]_i$ leads to a rise in intracellular calcium $[Ca^{2+}]_i$ level by affecting $Na^+/Ca^{2+}$ exchange. The increase in the $[Ca^{2+}]_i$ level results in a positive inotropic effect. Therefore, the positive inotropic effect is secondary to an increase in $[Na^+]$, after inhibition of the ($Na^+$+$K^+$)-ATPase. However, Jianye did not inhibit the ($Na^+$+$K^+$)-ATPase activity (FIG. 3) while increasing the force of contraction of the heart cells (FIG. 2A), indicating that the Jianye-induced positive inotropic effect is not coupled with the inactivation of the enzyme under our experimental conditions. Whether the binding of Jianye alters [Na$^+$]$_i$, we tested the effect of Jianye on [Na$^+$]$_i$ in CV-1 African Green monkey cells (American Type Culture Collection). Our study shows that the [Na$^+$]$_i$ was increased following the binding of Jianye, suggesting that the mechanistic pathway underlying Jianye-induced excitation/contraction involves the changes of [Na$^+$]$_i$. Both Jianye and digitalis glycosides bind to the (Na$^+$+K$^+$)-ATPase on the membrane surface and affect [Na$^+$l$_i$ and [Ca 2$^+$]$_i$ to increase the force of contraction. Whether they share a similar mechanistic pathway to alter [Na$^+$]$_i$ and [Ca 2$^+$]$_i$ through a Na$^+$/Ca$^{2+}$ exchanger remains to be determined. Nevertheless, the discovery that the Jianye antibody, as a potent non-inactivating inotropic reagent, provides new therapeutic strategies to improve the function of the failing heart in cardiovascular medicine.

Jianye antagonizes the ouabain binding by reducing the [$^3$H]ouabain labeling to the (Na$^+$+K$^+$)-ATPase (FIG. 11B). The specific peptide blocker (PB) eliminated this antagonist effect of Jianye (FIG. 11B) further emphasizing the specificity of Jianye in competitive [$^3$H]ouabain labeling. These results imply that the antigenic site of Jianye may contain one of the digitalis glycoside interacting-sites, located in the drug-binding pocket of the enzyme.

Example 6

Effect of the Zulan Antibody on Diastolic Ca$^{2+}$ Concentration

Figure 5:
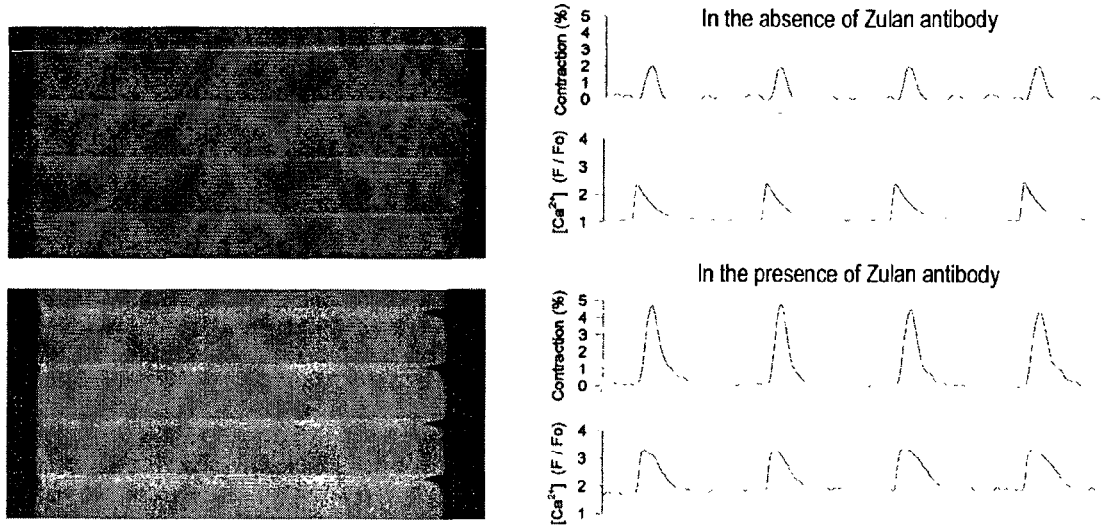
FIG. 5 shows the representative results of cell-contraction and intracellular $Ca^{2+}$ transient of the rat ventricular myocytes in the presence and absence of Zulan antibody. Left: The pictures (Fluo-4 fluorescence) represent the confocal linescan image of $[Ca^{2+}]_i$ transients. Time runs from top to bottom and the cell length is displayed horizontally. Right: Top traces represent time courses of cell shortening; bottom traces are averaged $Ca^{2+}$ transients, which were indexed by F/F0, where the F0 is the diastolic fluorescent level. $[Ca^{2+}]_i$ is expressed in arbitrary units, where resting $[Ca^{2+}]_1$ is 1, representing 100 nM $Ca^{2+}$. Contraction is expressed in percentage of the cell length. The results show that Zulan antibody increases cardiac myocytes contractility.

The Zulan antibody is specific for the amino acid sequence VPAISLAYEQAESD (SEQ ID NO: 2) of the (Na$^+$+K$^+$)-ATPase. As shown in FIG. 5 the Zulan antibody strikingly enhanced diastolic Ca$^{2+}$ concentration, but decreased diastolic cell length as seen in the line scan image. The plots derived from this image show that Zulan antibody significantly increased the amplitude of the Ca$^{2+}$ transient and the velocity of shortening ventricular myocytes, indicating increases in the force of contraction of the myocytes. These results indicate that the Zulan antibody is an inotropic agent, which directly controls and regulates the force of contraction of cardiac myocytes. This is the first time that a particular region (VPAISLAYEQAESD) (SEQ ID NO: 2) of the (Na$^+$+K$^+$)-ATPase that directly controls cardiac contractile biological function has been identified.

What is claimed:

1. A method of producing a positive ionotropic effect in a mammalian host, comprising administering an antibody which binds to a peptide consisting of the amino acid sequence as set forth in either KRQPRNPKTDKLVNE (SEQ ID NO:1) or VPAISLAYEQAESD (SEQ ID NO:2), wherein said antibody binds $(Na^{+}+K^{+})$-ATPase.

2. The method of claim 1, wherein the daily dose of antibody is from 1 mg/kg body weight to about 100 mg/kg body weight or more.

3. The method of claim 1, further comprising monitoring the mammal's cardiac contractions for a positive ionotropic effect.

* * * * *

UNITED STATES PATENT AND TRADEMARK OFFICE
CERTIFICATE OF CORRECTION

PATENT NO. : 8,496,929 B2
APPLICATION NO. : 10/164363
DATED : July 30, 2013
INVENTOR(S) : Kai Y. Xu Page 1 of 1

It is certified that error appears in the above-identified patent and that said Letters Patent is hereby corrected as shown below:

In the Claims:

Column 29, lines 2 and 12, "ionotropic" should read --inotropic--.
Column 29, line 9, "1 mg/kg" should read --1 μg/kg--.

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Arg Gln Pro Arg Asn Pro Lys Thr Asp Lys Leu Val Asn Glu
 1               5                  10                  15

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Pro Ala Ile Ser Leu Ala Tyr Glu Gln Ala Glu Ser Asp
 1               5                  10

<210> SEQ ID NO 3
<211> LENGTH: 15
<212> TYPE: PRT
<213> ORGANISM: Rattus sp.

<400> SEQUENCE: 3

Lys Arg Gln Pro Arg Asn Pro Lys Thr Asp Lys Leu Val Asn Glu
 1               5                  10                  15

<210> SEQ ID NO 4
<211> LENGTH: 15
<212> TYPE: PRT
<213> ORGANISM: Homo sapiens

<400> SEQUENCE: 4
```

Lys Arg Gln Pro Arg Asn Pro Lys Thr Asp Lys Leu Val Asn Glu
1               5                   10                  15

<210> SEQ ID NO 5
<211> LENGTH: 15
<212> TYPE: PRT
<213> ORGANISM: Canis familiaris

<400> SEQUENCE: 5

Lys Arg Gln Pro Arg Asn Pro Lys Thr Asp Lys Leu Val Asn Glu
1               5                   10                  15

<210> SEQ ID NO 6
<211> LENGTH: 15
<212> TYPE: PRT
<213> ORGANISM: Sus scrofa

<400> SEQUENCE: 6

Lys Arg Gln Pro Arg Asn Pro Lys Thr Asp Lys Leu Val Asn Glu
1               5                   10                  15

<210> SEQ ID NO 7
<211> LENGTH: 15
<212> TYPE: PRT
<213> ORGANISM: Gallus sp.

<400> SEQUENCE: 7

Lys Arg Gln Pro Arg Asn Pro Lys Thr Asp Lys Leu Val Asn Glu
1               5                   10                  15

<210> SEQ ID NO 8
<211> LENGTH: 15
<212> TYPE: PRT
<213> ORGANISM: Rattus sp.

<400> SEQUENCE: 8

Lys Arg Gln Pro Arg Asn Ser Gln Thr Asp Lys Leu Val Asn Glu
1               5                   10                  15

<210> SEQ ID NO 9
<211> LENGTH: 15
<212> TYPE: PRT
<213> ORGANISM: Homo sapiens

<400> SEQUENCE: 9

Lys Arg Gln Pro Arg Asn Ser Gln Thr Asp Lys Leu Val Asn Glu
1               5                   10                  15

<210> SEQ ID NO 10
<211> LENGTH: 15
<212> TYPE: PRT
<213> ORGANISM: Rattus sp.

<400> SEQUENCE: 10

Lys Arg Gln Pro Arg Asn Pro Arg Thr Asp Lys Leu Val Asn Glu
1               5                   10                  15

<210> SEQ ID NO 11
<211> LENGTH: 15
<212> TYPE: PRT
<213> ORGANISM: Homo sapiens

<400> SEQUENCE: 11

Lys Arg Gln Pro Arg Asn Pro Arg Thr Asp Lys Leu Val Asn Glu
1               5                   10                  15